United States Patent [19]

Caruso

[11] Patent Number: 5,919,826
[45] Date of Patent: Jul. 6, 1999

[54] METHOD OF ALLEVIATING PAIN

[75] Inventor: Frank S. Caruso, Colts Neck, N.J.

[73] Assignee: Algos Pharmaceutical Corporation, Neptune, N.J.

[21] Appl. No.: 08/904,519

[22] Filed: Aug. 1, 1997

Related U.S. Application Data

[63] Continuation-in-part of application No. 08/736,369, Oct. 24, 1996, abandoned.

[51] Int. Cl.$^6$ .................................................. A61K 31/165
[52] U.S. Cl. ........................................... 514/629; 514/646
[58] Field of Search ..................................... 514/629, 646

[56] References Cited

U.S. PATENT DOCUMENTS

| 3,652,589 | 3/1972 | Flick et al. . |
| 5,336,691 | 8/1994 | Raffa et al. . |
| 5,516,803 | 5/1996 | Raffa . |

FOREIGN PATENT DOCUMENTS

| 0615749 | 9/1994 | European Pat. Off. . |
| 93/17673 | 9/1993 | WIPO . |
| 96/06822 | 3/1996 | WIPO . |

OTHER PUBLICATIONS

Price et al., "Effects of the combined oral administration of NSAIDS, and dextromethorphanon on behavioral symptons indicative of arthritic pain in rats", Pain vol. 68, No. 1, pp. 119–127 (1996).

Lehmann, "Tramadol for the Management of Acute Pain", Drugs vol. 47, No. S1, pp. 19–32 (1994).

Sefrin, "Therapie des akuten Schmerzes im Rahmen der Notfallmedizin", Notfallmedizin vol. 23, No. 4, pp. 148–156 (1997).

Lipman, "Analgesic Drugs for Neuropathic and Sympathetically Maintained Pain", Clinics in Geriatric Medicine–Pain Management, vol. 12, No. 3 Aug. 1996, pp. 501–515.

Bession, "La Complexité des aspects Physiopharmacologiques de la Douleur", Drugs vol. 53, No. 52, pp. 1–9 (1997).

*Primary Examiner*—Zohreh Fay
*Attorney, Agent, or Firm*—Dilworth & Barrese

[57] ABSTRACT

The analgesic effectiveness of an tramadol is significantly enhanced by administering tramadol with the administration of an analgesia-enhancer which is a nontoxic NMDA receptor blocker and/or a nontoxic substance that blocks at least one major intracellular consequence of NMDA receptor activation.

7 Claims, 4 Drawing Sheets

Sample Isobole

METHOD OF ALLEVIATING PAIN

CROSS REFERENCE TO RELATED APPLICATION

This is a continuation-in-part of application Ser. No. 08/736,369 filed Oct. 24, 1996 now abandoned.

BACKGROUND OF THE INVENTION

This invention relates to a method of alleviating pain. More particularly, this invention is directed to a method of alleviating pain, e.g., arthritic pain, lumbosacral pain, musculo-skeletal pain, pain associated with a sore throat, etc., by administering to a mammal in need of relief from pain tramadol and, to enhance the analgesic effectiveness of the tramadol, a nontoxic antagonist for the N-methyl-D-aspartate (NMDA) receptor such as dextromethorphan, dextrorphan or ketamine.

The compound cis-2-[(dimethylamino)methyl]-1-(3-methoxyphenyl)cyclohexanol, commonly known as tramadol, is an analgesic commercially available as the hydrochloride salt. The process by which tramadol may be made is described in U.S. Pat. No. 3,652,589 the contents of which are incorporated herein by reference. Tramadol is chemically unrelated to the opiates, e.g., morphine, codeine, hydrocodone and oxycodone. However, a number of adverse side effects associated with the administration of tramadol, e.g., dizziness, somnolence, nausea, constipation, sweating and pruritus, are similar to that of the opioids. Since tramadol causes significantly less respiratory depression than the opioids, any enhancement, or potentiation, of the analgesic activity of tramadol would allow the dosage level of the drug to be reduced below that of the standard dosage level without a reduction in analgesic response. Alternatively, potentiation of tramadol would allow the standard dosage level to be maintained but with an increase in analgesic response. Either way, the safety of tramadol-induced analgesia will have been considerably improved by a potentiation of its analgesic effectiveness.

Dextromethorphan is the d-isomer of the codeine analog of levorphanol. Unlike the l-isomer, dextromethorphan is said to have no analgesic or addictive properties (Goodman and Gilman's, "The Pharmacological Basis of Therapeutics", 8th ed., McGraw-Hill, Inc. (1990), p. 518).

U.S. Pat. No. 5,336,691 describes an analgesic composition containing tramadol and acetaminophen alone, optionally in combination with an antitussive agent such as dextromethorphan, caraminophen and acceptable salts thereof.

Heretofore, there has been no recognition or appreciation that the analgesic effectiveness of tramadol can be appreciably enhanced by administration of tramadol prior to, with or following the administration of an analgesia-enhancing amount of dextromethorphan or for that matter, any other NMDA receptor antagonist.

SUMMARY OF THE INVENTION

In accordance with the present invention there is provided a method of alleviating pain which comprises administering to a mammal exhibiting pain other than pain associated with a cough condition (a) an analgesia-inducing amount of tramadol and (b) an analgesia-enhancing amount of at least one analgesia-enhancer selected from the group consisting of nontoxic antagonist for the N-methyl-D-aspartate receptor and nontoxic substance that blocks a major intracellular consequence of N-methyl-D-aspartate receptor activation.

The method of the invention is applicable to the treatment of all varieties of pain with the sole exception of pain associated with cough. Thus, for a mammal in need of pain relief but not exhibiting a cough condition, an enhanced level of analgesia for an equivalent dosage of tramadol, or an equivalent level of analgesia for a reduced dosage of tramadol, can be achieved when the tramadol is administered prior to, with or following the administration of the analgesia-enhancer.

The term "tramadol" shall be understood to include the free base of tramadol as well as its pharmaceutically acceptable acid addition salts.

The expression "N-methyl-D-aspartate receptor" shall be understood to include all of the binding site subcategories associated with the NMDA receptor, e.g., the glycine-binding site, the phenylcyclidine (PCP)-binding site, etc., as well as the NMDA channel. Thus, the invention herein contemplates the use of nontoxic substances that block an NMDA receptor binding site, e.g., dextrorphan, or the NMDA channel, e.g., a source of magnesium such as magnesium sulfate.

The term "nontoxic" as used herein shall be understood in a relative sense and is intended to designate any substance that has been approved by the United States Food and Drug Administration ("FDA") for administration to humans or, in keeping with established regulatory criteria and practice, is susceptible to approval by the FDA for administration to humans. The term "nontoxic" is also used herein to distinguish the NMDA receptor antagonists, or blockers, that are useful in the practice of the present invention from NMDA receptor antagonists such as MK 801 (the compound 5-methyl-10,11-dihydro-SH-dibenze[a,d] cyclohepten-5,10-imine), CPP (the compound 3-[2-carboxypiperazin-4-yl] propyl-1-phosphonic acid) and PCP (the compound 1-(1-phenylcyclohexyl)piperidine) whose toxicities effectively preclude their therapeutic use.

The term "pain-alleviating" shall be understood herein to include the expressions "pain-suppressing" and "pain-inhibiting" as the invention is applicable to the alleviation of existing pain as well as the suppression or inhibition of pain which would otherwise ensue from an imminent pain-causing event.

The expression "analgesia-enhancing" shall be understood herein to mean the ability of the analgesia-enhancer to increase, potentiate, or synergize the analgesic effectiveness of tramadol beyond that which would be expected based on the analgesic effectiveness of tramadol alone and the analgesic effectiveness of the analgesia-enhancer alone as determined by the measurement of mechanical hyperalgesia in the arthritic rat (the Randall-Sellito Test, described infra). Such unexpected increase in the analgesic effectiveness of tramadol can therefore be considered to be one of synergy brought about by the administration of the analgesic enhancer in accordance with this invention.

DESCRIPTION OF THE PREFERRED EMBODIMENTS

Figure 1:
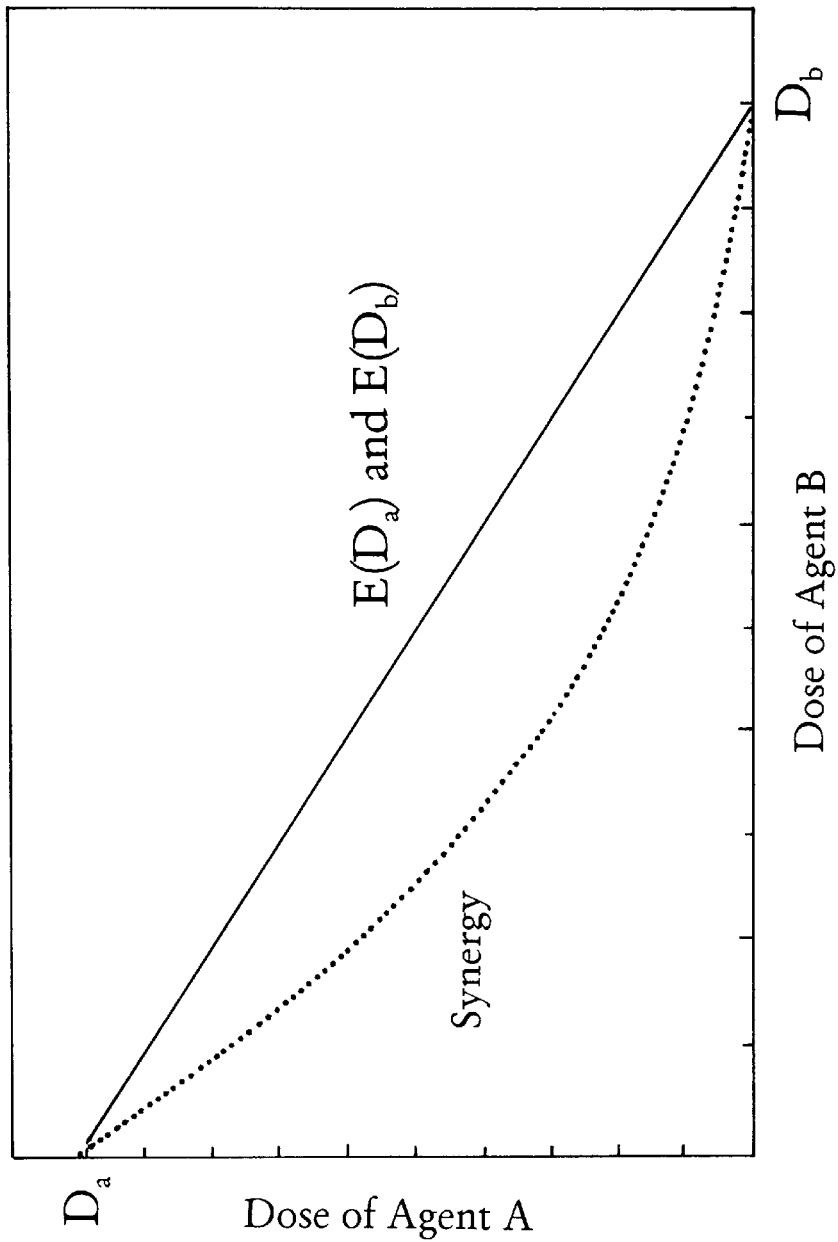
FIG. 1 is a graph of a sample isobole for two drug agents A and B illustrating the general principles by which a drug combination can be determined to be synergistic or not.

Among the nontoxic substances that block the NMDA receptor and as such are useful for enhancing the analgesic activity of tramadol in accordance with this invention are dextromethorphan ((+)-3-hydroxy-N-methylmorphinan) and its metabolite dextrorphan ((+)-3-hydroxy-N-methylmorphinan), their mixtures and their pharmaceutically acceptable salts. Other useful nontoxic substances that block the NMDA receptor include amantadine (1-aminoadamantine), memantine (3,5-dimethylaminoadamantone), pyrroloquinoline quinone and cis-4-(phosphonomethyl)-2-piperidinecarboxylic acid. Of the NMDA receptor antagonists, dextromethorphan in the form of its hydrobromide salt is preferred for use herein due to its high degree of proven safety and its ready availability. While dextrorphan and its pharmaceutically acceptable salts will also provide excellent results, it is not known to be in commercial manufacture at this time.

In addition to, or in place of, a blocker for the NMDA receptor, at least one nontoxic substance that blocks a major intracellular consequence of NMDA receptor activation can also be used as the analgesia-enhancer herein. Activation of the NMDA receptor, a subtype of excitatory amino acid receptors, induces a number of changes in the functional activity of nerve cells and, in particular, their capacity for excitability or inhibition in the presence of an addictive substance via an increase in intracellular Ca++ concentration. The major consequences of NMDA receptor activation include the following sequences, or cascades, of events occurring within nerve cells:

a) translocation and activation of protein kinases such as protein kinase C→phosphorylation of substrate proteins such as cytosolic enzymes, channel proteins, receptor proteins, etc.→changes in functional activity;

b) initiation of early gene (c-fos, c-jun, zif-268, etc.) expression by either increased intracellular Ca++ or Ca++-activated protein kinases→expression of functional genes responsible for production of cellular enzymes (such as protein kinases), receptor proteins (such as the NMDA receptor), ion channel proteins (such as K+, Na+, Ca++ channels), neuropeptides (such as dynorphin), etc.→changes in functional activity;

c) Ca++/calmodulin (or other Ca++ binding proteins) induced activation of enzymes and other cellular components→activation of Ca++/calmodulin-protein kinase systems such as Ca++/calmodulin kinase II→autophosphorylation of enzymes (e.g., Ca++/calmodulin kinase II) or other functional proteins→changes in functional activity;

d) Ca++/calmodulin induced activation of constitutive nitric oxide synthase as well as induction of inducible nitric oxide synthase→production of nitric oxide→i) production of cyclic guanosine monophosphate via activation of guanosine cyclase resulting in activation of protein kinases and early gene expression; ii) direct protein modification such as enzymes, receptor and/or channel proteins; iii) lipid membrane modification and/or nucleic acid modification via scavenge of free radicals; iv) induction of neurotoxicity at higher nitric oxide levels; v) retrograde actions in adjacent neurons or glial cells such as facilitation of glutamate release/NMDA receptor activation and/or inhibition of post-synaptic NMDA receptors→changes in functional activity;

e) interactions with the cyclic adenosine monophosphate/protein kinase A system, the phospholipase C-inositol triphosphate-Ca++/diacylglycerol-protein kinase system, the phospholipase A2-arachidonic acid/prostanoids/leukotrienes system→changes in functional activity induced by second messenger systems other than NMDA receptor/$Ca^{++}$/$Ca^{++}$-calmodulin/protein kinase systems; and, f) interactions with other excitatory amino acid receptor subtypes including non-NMDA receptors and metabotropic receptors as well as intracellular events subsequent to the activation of these excitatory amino acid receptor subtypes→changes in functional activity induced by the non-NMDA and metabotropic receptor activation.

A substance that blocks the NMDA receptor will effectively prevent all of the foregoing major intracellular sequences of events from taking place. However, even with activation of the NMDA receptor, it is still possible to treat pain in accordance with this invention by administering the tramadol and a substance that blocks at least one of the foregoing major intracellular sequences of events. Thus, e.g., a substance that interferes with translocation and activation of protein kinase C or with calmodulin induced activation of constitutive nitric oxide synthase as well as induction of inducible nitric oxide synthase is also useful for the practice of this invention.

Nontoxic substances that block a major intracellular consequence of NMDA receptor activation and are therefore useful in the practice of the invention include inhibitors of protein kinase C, e.g., gangliosides such as ganglioside $GM_1$ (monosialoganglioside) and ganglioside $GT_{1b}$ (trisialoganglioside); amphipathic long chain bases such as sphingosine, N,N,N-trimethylsphingosine, sphinganine and psychosine; quinolyloxazole-2-ones such as 4-methyl-5-(3-quinolinyl)-2-(3H)-oxazolone and phenyl-5-(2-quinolinyl)-2-3(3H)-oxazolone; 1,4-bis-(aminohydroxyalkylamino)-anthraquinones such as 1,4-bis-(3-propylamino-2-hydroxypropylamino)-9,10 anthracenedione and 1,4-bis-(3-benzylamino-2-hydroxypropylamino)-9,10 anthracenedione; and, mixtures and pharmaceutically acceptable salts of any of the foregoing.

Additional nontoxic substances that block a major intracellular consequence of NMDA receptor activation and as such are useful in the practice of the invention include inhibitors of calmodulin such as the phenothiazines, in particular, chlorpromazine, chlorpromazine sulfoxide, prochlorperazine dimaleate, perphenazine, trifluoperazine, fluphenazine, fluphenazine enanthate, fluphenazine decanoate, thioridazine, mesoridazine besylate, piperacetazine, acetophenazine dimaleate, carphenazine dimaleate, butaperazine dimaleate and phenothiazine sulfoxide; naphthalenesulfonamides such as N-(6-aminohexyl)-5-chloro-1-naphthalenesulfonamide, N-(6-aminohexyl)-5-chloro-2-naphthalenesulfonamide and N-(6-aminohexyl)-5-bromo-2-naphthalenesulfonamide; 4-substituted-4H,6H-pyrrolo[1,2-a] [4,1] benzoxazepines such as 1,3-dihydro-1-{1-[(4-methyl-4H,6H-pyrrolo[1,2-a] [4,1] benzoxazepin-4-yl)methyl)-4-piperidinyl}-2H- benzimidazol-2-one; benzhydryls such as N-[2] (diphenylmethylthioethyl]-2-(trifluoromethyl)-benzeneethanamine, N-[2-(bis(4-fluorophenyl)methylthio)-ethyl]-2-(trifluoromethyl)benzeneethanamine and N-[2-(bis (4-fluorophenyl)methylthio)ethyl]-3-(trifluoromethyl) benzeneethanamine; tricyclic antidepressant drugs such as imipramine, 2-chloroimipramine and amitriptyline; penfluridol; haloperidol; pimozide; clozapine; calmidazolin; and, mixtures and pharmaceutically acceptable salts of any of the foregoing.

Of the two groups of analgesia-enhancers, the NMDA-receptor antagonists are preferred and of these, dextromethorphan is preferred for the reasons previously stated.

Dosage levels for the tramadol will, of course, be those sufficient to induce an effective degree of analgesia. Thus, e.g., for adult humans, typical unit dosage levels of tramadol can vary from about 50 to about 100 mg. Dosage levels for tramadol which are greater or lesser than these can, of course, be employed if desired.

To exhibit its analgesic activity-enhancing effect, the nontoxic NMDA receptor antagonist and/or substance that blocks a major intracellular consequence of NMDA receptor activation must be present in an analgesia-enhancing amount. This amount can be experimentally determined for a given substance of this type by those skilled in the art employing routine dosage determination procedures in view of the experimental data herein. In the case of the NMDA receptor antagonist dextromethorphan, a usual recommended dose for adult humans would be at least about 30 mg and preferably at least about 60 to 120 mg. Unit dosages can contain less than these amounts of dextromethorphan provided, of course, sufficient multiples of the unit dose are administered at one time to provide the aforestated minimum dextromethorphan dose. Thus, e.g., one or two tablets each containing 50 mg tramadol and approximately 30 mg dextromethorphan can be administered at one time (up to 8 times in a 24 hour period) to provide enhanced analgesia in accordance with the present invention.

While the tramadol and the analgesia-enhancer need not be administered together, they must both be present in the patient at effective levels at the same time. While it is within the scope of the invention to administer tramadol and analgesia-enhancer separately, as a matter of convenience, it is preferred that they be coadministered as a single therapeutic composition. All modes of administrations are contemplated, e.g., administration can be orally, rectally or by intravenous, intramuscular, subcutaneous, intrathecal, epidural or intracerebro-ventricular injection.

A therapeutic composition containing tramadol and the analgesia-enhancer will ordinarily be formulated with one or more pharmaceutically acceptable ingredients in accordance with known and established practice. Thus, the composition can be formulated as a liquid, powder, elixir, injectable solution, etc. Formulations for oral use can be provided as tablets or hard capsules wherein the pharmacologically active ingredients are mixed with an inert solid diluent such as calcium carbonate, calcium phosphate or kaolin, or as soft gelatin capsules wherein the active ingredients are mixed with an oleaginous medium, e.g., liquid paraffin or olive oil.

Aqueous suspensions can include pharmaceutically acceptable excipients such as suspending agents, e.g., sodium carboxymethyl cellulose, methylcellulose, hydroxypropylmethylcellulose, sodium alginate, polyvinylpyrrolidone, gum tragacanth and gum acacia; dispersing or wetting agents such as naturally occurring phosphatide, e.g., lecithin, or condensation products of an alkylene oxide with fatty acids, e.g., polyoxyethylene stearate, or condensation products of ethylene oxide with long chain aliphatic alcohols, e.g, heptadecaethyleneoxycetanol, or condensation products of ethylene oxide with partial esters derived from fatty acids and a hexitol, e.g., polyoxyethylene sorbitol monoleate or condensation products of ethylene oxide with partial esters derived from fatty acids and hexitol anhydrides, e.g., polyoxyethylene sorbitan monoleate. The aqueous suspensions can also contain one or more preservatives, e.g., ethyl-or-n-propyl-p-hydroxy benzoate, one or more coloring agents, one or more flavoring agents and one or more sweetening agents, such as sucrose, saccharin or sodium or calcium cyclamate.

In addition to tramadol and analgesia-enhancer, the therapeutic composition herein can contain at least one other pharmacologically active substance e.g., acetaminophen, a nonsteroidal anti-inflammatory drug such as aspirin, diclofenac, diflusinal, etodolac, fenbufen, fenoprofen, flufenisal, flurbiprofen, ibuprofen, indomethacin, ketoprofen, ketorolac, meclofenamic acid, mefenamic acid, nabumetone, naproxen, oxaprozin, phenylbutazone, piroxicam, sulindac, tolmetin, zomepirac, and the like, a narcotic analgesic such as codeine, oxycodone, and the like, or a local anesthetic such as lidocaine, dibucaine, bupivicaine and the like (where the composition is provided as an injectable).

The following example is illustrative of the method of the invention in alleviating arthritic pain induced in the Sprague-Dawley rat.

EXAMPLE

A. Synergy and the Method of Isoboles

A synergistic combination of two drug agents is defined as a combination which has an effectiveness that is greater than that which would be expected on the basis of the effectiveness of the individual drugs alone. As explained and demonstrated by Berenbaum, "What is Synergy?" *Pharmacological Reviews*, v. 41, p.93, (1989), the only generally valid method of determining the expected effect of a combination of drug agents is the experimental determination of equi-effective doses, or "Method of Isoboles" as it is more commonly called. Reference may be made to Berenbaum for a complete derivation of, and rationale for, the Method of Isoboles. Assuming that a combination of two different drug agents (Agent A and Agent B) is being studied, the Method of Isoboles generally requires a knowledge of the dose response curve of each agent acting singly. In addition, the effectiveness of some fixed combination of dose $d_a$ of Agent A and dose $d_b$ of Agent B is determined. From the dose response curves of Agent A alone, the dose of A which is equi-effective with the combination, designated $D_a$, is determined. Similarly, from the dose response curve of Agent B alone, designated $D_b$, the dose of B alone which is equi-effective with the combination is determined. In this way $D_a$, $D_b$, and the combination of doses $d_a$ of A and $d_b$ of B all produce the same level of efficacy.

On the Sample Isobole shown in FIG. 1 where the vertical axis represents doses of agent A and the horizontal axis represents doses of agent B, points ($D_a$,0) and (0,$D_b$) are connected with a straight line. If the doses ($d_a$ $d_b$) used in the combination when graphed as the point ($d_a$,$d_b$) fall on the line connecting $D_a$ and $D_b$, then the combination is concluded to be neither synergistic nor antagonistic. If, however, the point ($d_a$,$d_b$) falls to the left of and below the line joining $D_a$ and $D_b$ (as in the dotted line), then smaller doses of A and B in combination are required to achieve the same level of effectiveness based on the levels of effectiveness of A acting alone and B acting alone. This indicates that the combination of A and B is synergistic.

Theoretically, any point which falls below the isobole joining $D_a$ and $D_b$ even by only a small amount represents synergy. In practice, the actual level of effectiveness of drugs acting alone or in combination cannot be known exactly. These levels of average efficacy can only be estimated up to the precision of a given experimental assay. In attempting to decide whether the results of an assay provide positive evidence of synergy, some method must be used which judges the sizes of differences between treatments against the level of variability seen in the data. Statistical tests of significance provide a rule for deciding, based on an analysis of experimental data, whether conclusions about real differences among treatments included in the evaluation of two drugs and their combinations can be made. Tests of significance generally involve calculation of two quantities: (a) a test statistic which measures the size of differences among treatments against the precision with which these differences are estimated and (b) the level of significance of the test statistic.

The smaller the level of significance the less likely it is that treatments which are in fact equal in effectiveness could have generated as large a difference as was observed. In fact, the level of significance is actually a probability. Specifically, it is the probability that, assuming the treatments being compared are equal, the test statistic comparing them could be at least as large as its observed value. A test of statistical significance rejects the null hypothesis of equality of treatments being compared if this probability, or level of significance, is small. As stated in Cochran et al., "Experimental Designs" (John Wiley and Sons, New York, 1957), 0.05 is a commonly used cut-off value for determining statistical significance. Using the $P<0.05$ cut-off value, treatments whose tests of significance generate significance levels less than 0.05 are generally considered to be significantly different.

Figure 2:
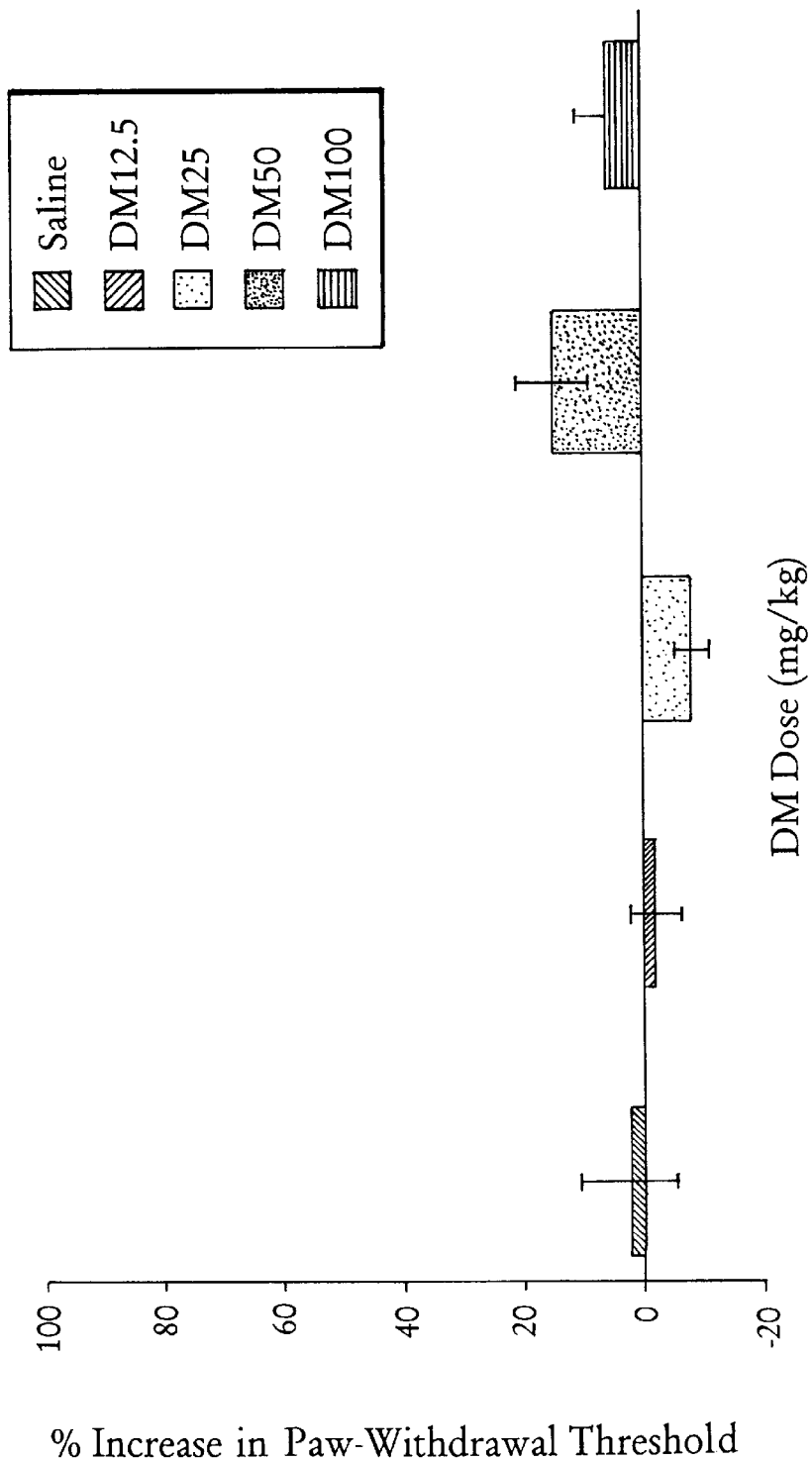
FIG. 2 is a bar graph comparing the different scores for mechanical hyperalgesia, an indicator of arthritic pain, observed in laboratory animals with induced arthritis both before and following oral administration of dextromethorphan hydrobromide alone at various levels and saline alone.
Figure 3:
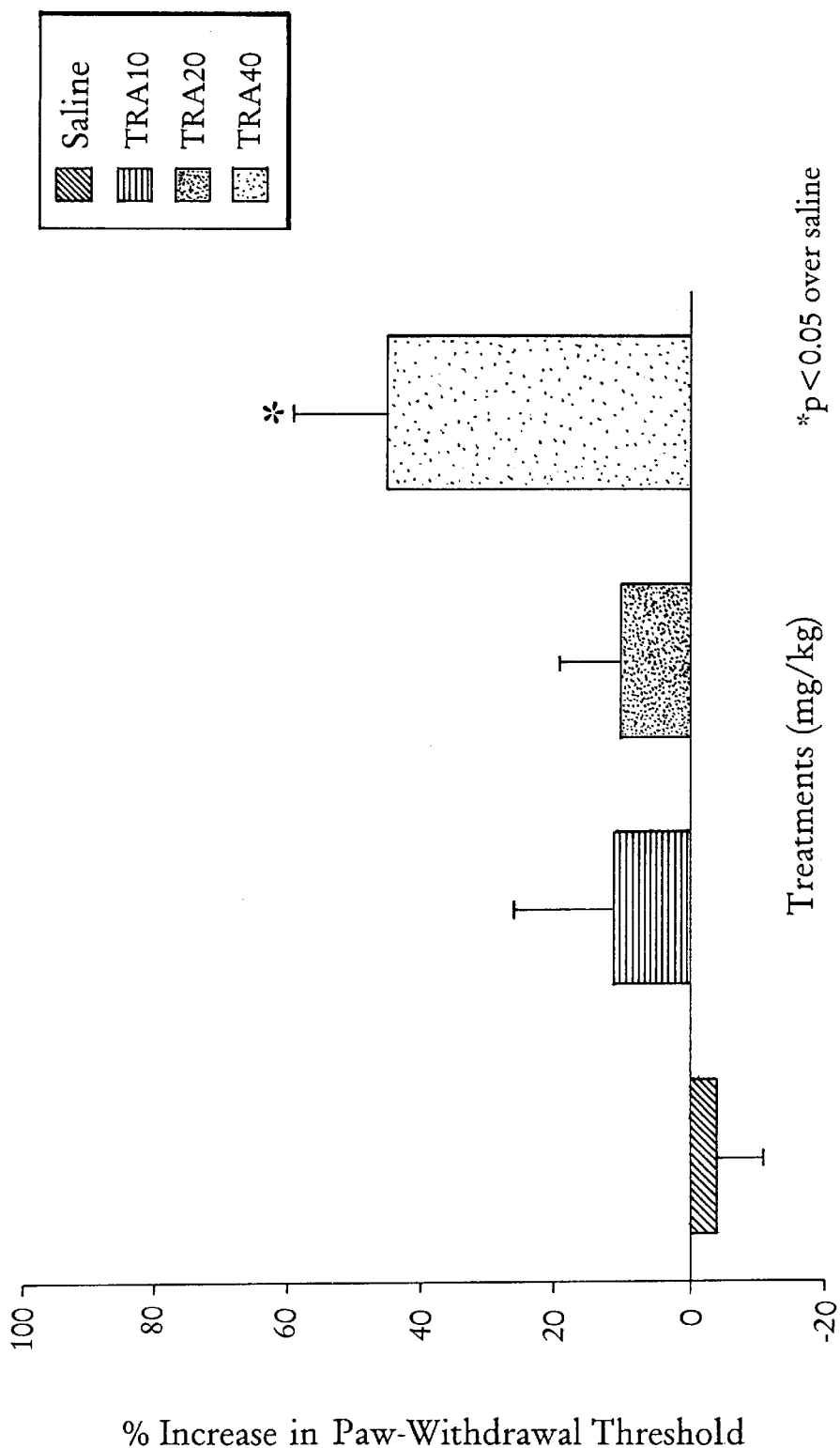
FIG. 3 is a bar graph comparing the different scores for mechanical hyperalgesia observed in laboratory animals with induced arthritis both before and following oral administration of tramadol alone at various levels and saline alone.
Figure 4:
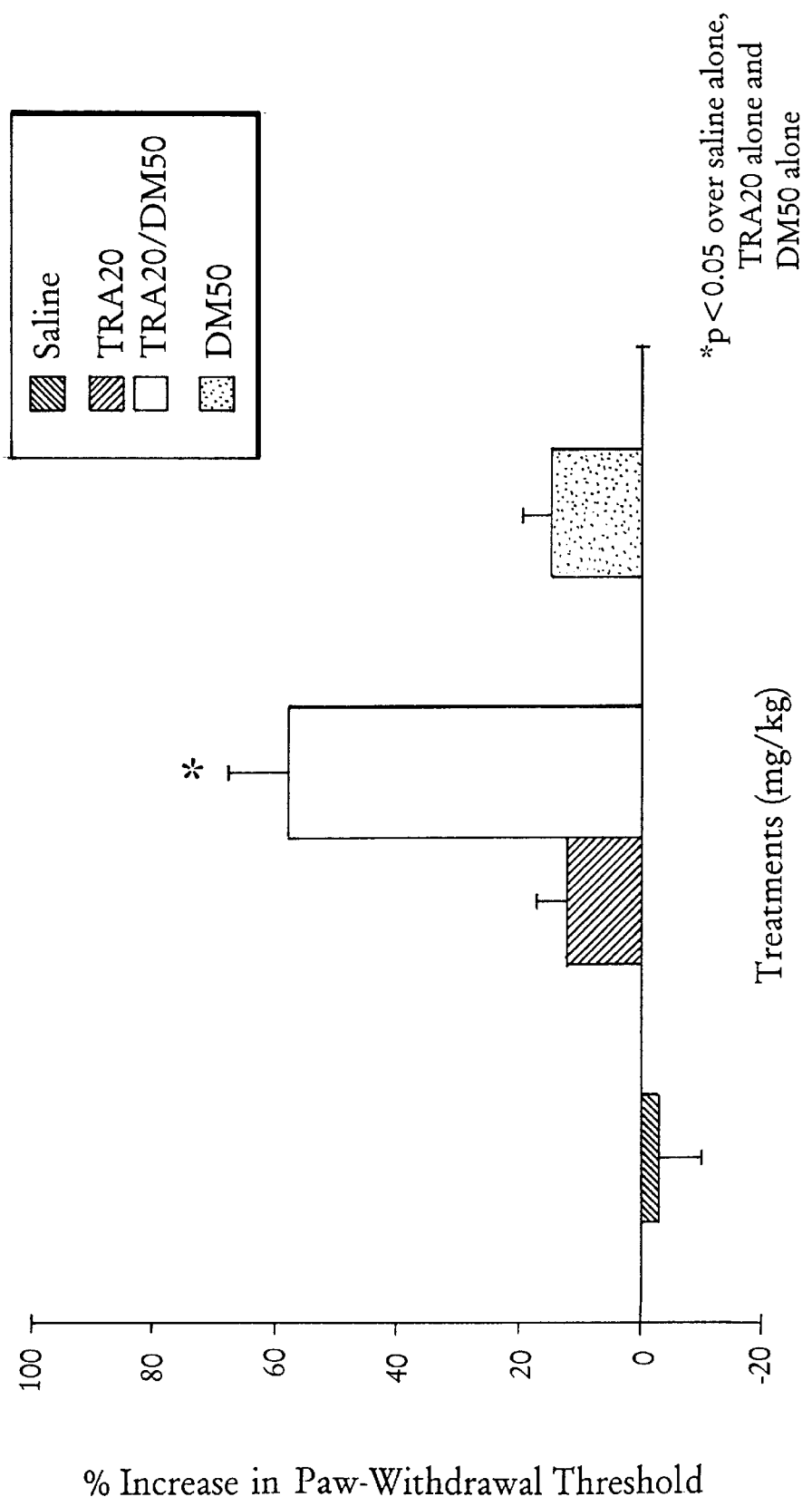
FIG. 4 is a bar graph comparing the different scores for mechanical hyperalgesia observed in laboratory animals with induced arthritis both before and following oral administration of saline alone, tramadol alone and tramadol in combination with dextromethorphan hydrobromide.

As required by the aforedescribed Method of Isoboles, assays estimating the level of effectiveness of a range of doses of both tramadol (TRA) and dextromethorphan hydrobromide (DM) administered alone were conducted. One combination of doses was also studied. FIGS. 2–4 summarize the results of these assays.

In the graphs of FIGS. 2–4, the heights of the bars correspond to the average level of effectiveness estimated by the assay for that treatment. The length of the line running from the top of the bar provides a measure of the precision of the estimated average level of effectiveness. Shorter lines represent less variability in the data and, therefore, greater confidence that the true average effectiveness of that treatment is close to the estimated average. Longer lines mean greater variability. In addition, those bars are that annotated with an asterisk "*" indicate statistically meaningful drug response using the aforesaid significance level of 0.05. In FIG. 2, none of the doses of DM exhibited statistically significant analgesia over saline according to the assay method employed (the Randall-Sellito Test described below). In FIG. 3, of the various doses of TRA evaluated, only the TRA 40 dose was observed to possess statistically significant analgesia over saline. In FIG. 4, only the TRA 20/DM 50 dose was observed to possess statistically significant analgesia over saline alone, TRA 20 alone and DM 50 alone. These results are disclosed in greater detail below.

B. Test Procedures

Arthritic pain (monarthritis) was induced in the test rats by intracapsual injection of a complete adjuvant (Butler et al., *Pain,* 48 (1992), pp. 73–81). The complete adjuvant was made up of 60 mg killed *Mycobacterium butyricum* in a mixture of paraffin oil (6 ml), 0.9% NaCl (4 ml) and Tween 80 (1 ml). The rats were briefly anesthetized with isoflurane administered in a mixed $N_2O/O_2$ gas. A drop of complete adjuvant (about 0.05 ml) was injected into the ankle (tarsotibial) joint with a 26 gauge needle. Monarthritic pain develops in about 7 days after injection and peaks after about two weeks (Butler et al. ibid.).

The following behavioral test of arthritic pain was made at 14 days after the injection of complete adjuvant to establish baseline scores for the test as described in the literature (Butler et al., ibid.; Perrot et al., *Pain,* 52 (1993), pp. 41–47).

Mechanical Hyperalgesia

The Randall-Sellito test was used to examine mechanical hyperalgesia (Butler et al., ibid.; Perrot et al., ibid.). A graded mechanical force (in grams) delivered through the Randall-Selitto device was applied to the affected ankle areas. A rat withdrew its hindpaw or vocalized when the applied force reached its pain threshold. This force was recorded to indicate the degree of mechanical hyperalgesia.

After determination of the baseline scores for this test, each rat received an oral dose of the following test substances: (1) TRA alone at various levels, (2) DM alone at various levels, (3) a combination of TRA at 20 mg/kg and DM at 50 mg/kg, (4) saline (control) alone. At 1.5 hours after each administration, the behavioral test described above was repeated to examine the effects of each test substance on arthritic pain.

C. Test Results

FIGS. 2, 3 and 4 graphically present the data obtained from the foregoing assays. The data were analyzed using separate 2×2 factorial analysis of variance. Comparisons between individual pairs of treatments were conducted using the Waller-Duncan K ratio t test ("SAS Procedures Guide", Version 6, 34d ed., SAS Institute Inc., Cary, N.C. (1990), pp. 705 et seq.), with the pooled error mean square from the factorial analysis of variance as the denominator.

FIG. 2: Mechanical Hyperalgesia with DM alone

The percent change of paw-withdrawal thresholds before and after administration of DM alone at various levels and saline alone was used to express the degree of mechanical hyperalgesia. When tested at 1.5 hours after administration of the test substances, paw-withdrawal thresholds were not reduced to any statistically meaningful degree in rats receiving a single oral administration of DM at any of the 12.5, 25, 50 and 100 mg/kg dosage levels tested as compared to the saline controls. These results show that when administered by itself, DM has no significant analgesic effectiveness as determined by the Randall-Sellito Test.

FIG. 3: Mechanical Hyperalgesia with TRA alone

The percent change of paw-withdrawal thresholds before and after administration of TRA alone at various levels and saline alone was used to express the degree of mechanical hyperalgesia. When tested at 1.5 hours after administration of the test substances, paw-withdrawal thresholds were not reduced to any statistically meaningful degree in rats receiving a single oral administration of 10 and 20 mg/kg TRA as compared to the saline controls. However, oral administration of TRA at 40 mg/kg resulted in a statistically meaningful (*=$P<0.05$ as compared to the saline controls) increase in paw-withdrawal thresholds demonstrating a significantly enhanced analgesic effect as determined by the Randall-Sellito Test.

FIG. 4: Mechanical Hyperalgesia with the TRA/DM Combination

The percent change of paw-withdrawal thresholds before and after administration of each test substance was used to express the degree of mechanical hyperalgesia. When tested at 1.5 hours after administration of the test substances, paw-withdrawal thresholds were not reduced to any statistically meaningful degree in rats receiving a single oral administration of 10 mg/kg and 20 mg/kg TRA but were reduced to a statistically meaning (*=P<0.05 as compared to the saline controls alone) in the rats which received the 40 mg/kg dose. Oral administration of TRA (20 mg/kg) in combination with DM (50 mg/kg) also resulted in a statistically meaningful (*=P<0.05 as compared to the saline controls alone) increase in paw-withdrawal thresholds demonstrating a significantly enhanced therapeutic effect for the combination of TRA and DM as determined by the Randall-Sellito Test. Given the fact that 120 mg/kg and 20 mg/kg dosages of TRA alone provided no statistically meaningful analgesia and further given the fact that DM at any of the dosage levels administered provided no statistically meaningful analgesia, it was entirely unexpected and surprising that the combination of 20 mg/kg TRA and 50 mg/kg DM should have any statistically significant analgesia and, moreover, a level of analgesia which was comparable, if not superior, to that of the 40 mg/kg TRA dosage.

What is claimed is:

1. A method of alleviating pain which comprises administering to a mammal exhibiting pain other than pain associated with a cough condition (a) tramadol and (b) a tramadol analgesia-enhancing, but essentially sub-analgesic, amount of at least one tramadol analgesia-enhancer selected from the group consisting of dextromethorphan, dextrorphan and pharmaceutically acceptable salt thereof, the total amount of (a) and (b) administered being an effective analgesic amount.

2. The method of claim 1 wherein (a) and (b) are coadministered as a single dosage form.

3. The method of claim 2 wherein (a) and (b) are coadministered as a sustained release dosage form.

4. The method of claim 1 wherein the pain is due to an arthritic condition.

5. The method of claim 1 further comprising a therapeutically effective amount of at least one other pharmacologically active substance (c).

6. The method of claim 5 wherein pharmacologically active substance (c) is selected from the group consisting of acetaminophen, nonsteroidal anti-inflammatory drug, narcotic analgesic and local anesthetic.

7. The method of claim 2 wherein the amount of coadministered tramadol is, when administered by itself, an essentially sub-analgesic amount.

* * * * *